(12) United States Patent
Shartle et al.

(10) Patent No.: US 6,875,613 B2
(45) Date of Patent: *Apr. 5, 2005

(54) BIOLOGICAL FLUID CONSTITUENT SAMPLING AND MEASUREMENT DEVICES AND METHODS

(75) Inventors: Robert Shartle, Livermore, CA (US); Koon-wah Leong, Sunnyvale, CA (US); Ernest J. Kiser, Los Altos, CA (US)

(73) Assignee: LifeScan, Inc., Milpitas, CA (US)

( * ) Notice: Subject to any disclaimer, the term of this patent is extended or adjusted under 35 U.S.C. 154(b) by 341 days.

This patent is subject to a terminal disclaimer.

(21) Appl. No.: 09/879,188

(22) Filed: Jun. 12, 2001

(65) Prior Publication Data

US 2002/0187556 A1 Dec. 12, 2002

(51) Int. Cl.[7] .............................................. G01N 33/48
(52) U.S. Cl. ......................... 436/63; 436/150; 436/95; 422/61; 422/76; 422/68.1; 422/150; 604/318; 604/404; 604/411; 604/412
(58) Field of Search ........................... 422/58, 61, 7–6, 422/68.1, 82.05; 436/63, 91, 95, 164, 165, 150; 604/317, 318, 403, 404, 411, 412

(56) References Cited

U.S. PATENT DOCUMENTS

| | | | |
|---|---|---|---|
| 4,671,288 A | * 6/1987 | Gough | 600/347 |
| 5,161,532 A | 11/1992 | Joseph | |
| 5,582,184 A | 12/1996 | Erickson et al. | |
| 5,746,217 A | 5/1998 | Erickson et al. | |
| 5,879,310 A | 3/1999 | Sopp et al. | |
| 5,879,367 A | 3/1999 | Latterell et al. | |
| 5,897,522 A | * 4/1999 | Nitzan | 604/20 |
| 5,942,102 A | 8/1999 | Hodges et al. | |
| 6,080,116 A | 6/2000 | Erickson et al. | |
| 6,083,196 A | 7/2000 | Trautman et al. | |
| 6,091,975 A | 7/2000 | Daddona et al. | |
| 6,162,611 A | 12/2000 | Heller et al. | |
| 6,379,324 B1 | 4/2002 | Gartstein et al. | |

FOREIGN PATENT DOCUMENTS

| | | |
|---|---|---|
| WO | WO 97/00441 | 1/1997 |
| WO | WO 97/42888 | 11/1997 |
| WO | WO 98/00193 | 1/1998 |
| WO | WO 908/34541 | 8/1998 |
| WO | WO 99/13336 | 3/1999 |
| WO | WO 99/27852 | 6/1999 |
| WO | WO 99/64580 | 12/1999 |
| WO | WO 00/35530 | 6/2000 |
| WO | WO 00/45708 | 8/2000 |
| WO | WO 00/57177 | 9/2000 |
| WO | WO 00/74763 | 12/2000 |
| WO | WO 00/74765 | 12/2000 |

* cited by examiner

Primary Examiner—Lyle A. Alexander
(74) Attorney, Agent, or Firm—Carol M. LaSalle; Bozicevic, Field & Francis, LLP

(57) ABSTRACT

A device for accessing biological fluid, sampling biological fluid constituents and determining the concentration of at least one target constituent within the accessed biological fluid is provided. The device has at least one micro-piercing member used to penetrate the skin to a selected depth and to access biological fluid, a constituent sampling means and a constituent measuring means. The constituent sampling means comprises a constituent transfer medium, such as a hydrophilic gel material, by which sampled constituents are transferred from the micro-piercing member to the measuring means. The measuring means includes an electrochemical cell having at least one porous electrode through which at least one sampled constituent is caused to enter into the electrochemical cell. Methods of sampling constituents within the skin and measuring the sampled constituents, as well as kits for practicing the invention are provided.

36 Claims, 2 Drawing Sheets

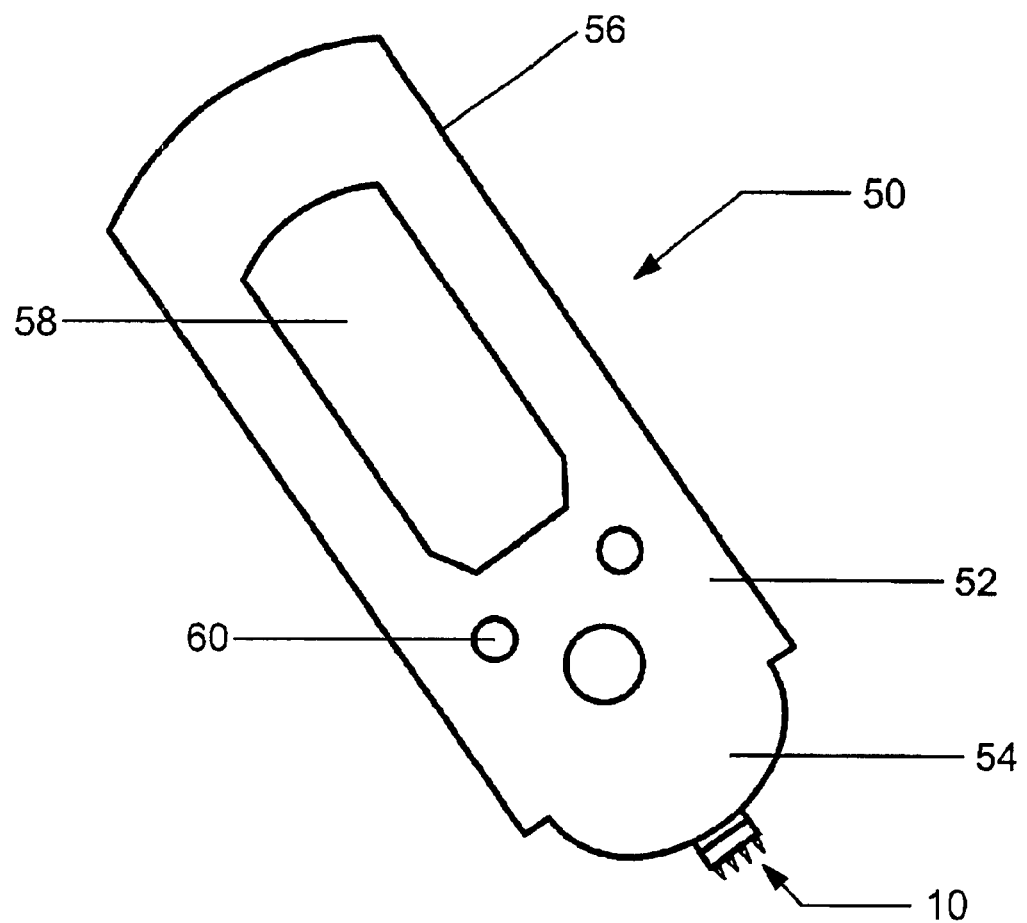

BIOLOGICAL FLUID CONSTITUENT SAMPLING AND MEASUREMENT DEVICES AND METHODS

FIELD OF THE INVENTION

This invention is related to percutaneous biological fluid constituent sampling and analyte measurement devices and methods.

BACKGROUND

The detection of analytes in biological fluids is of ever increasing importance. Analyte detection assays find use in a variety of applications, including clinical laboratory testing, home testing, etc., where the results of such testing play a prominent role in the diagnosis and management of a variety of disease conditions. Common analytes of interest include glucose, e.g., for diabetes management, cholesterol, and the like.

A common technique for collecting a sample of blood for analyte determination is to pierce the skin at least into the subcutaneous layer to access the underlining blood vessels in order to produce localized bleeding on the body surface. The accessed blood is then collected into a small tube for delivery and analyzed by testing equipment, often in the form of a hand-held instrument having a reagent test strip onto which the blood sample is placed. The fingertip is the most frequently used site for this method of blood collection due to the large number of small blood vessels located therein. This method has the significant disadvantage of being very painful because subcutaneous tissue of the fingertip has a large concentration of nerve endings. It is not uncommon for patients who require frequent monitoring of an analyte, to avoid having their blood sampled. With diabetics, for example, the failure to frequently measure their glucose level on a prescribed basis results in a lack of information necessary to properly control the level of glucose. Uncontrolled glucose levels can be very dangerous and even life-threatening. This technique of blood sampling also runs the risk of infection and the transmission of disease to the patient, particularly when done on a high-frequency basis. The problems with this technique are exacerbated by the fact that there is a limited amount of skin surface that can be used for the frequent sampling of blood.

To overcome the disadvantages of the above technique and others that are associated with a high degree of pain, certain analyte detection protocols and devices have been developed that use micro-piercing, micro-cutting elements or analogous structures to access the interstitial fluid within the skin. The micro-needles are penetrated into the skin to a depth less than the subcutaneous layer so as to minimize the pain felt by the patient. The interstitial fluid is then sampled and tested to determine the concentration of the target analyte.

Conventional micro-needle sampling systems have a drawback in that, because the interstitial fluid inside the human body is at a negative pressure of about 6 mm/Hg, some kind of mechanical or vacuum means is often used in conjunction with the micro-piercing members.

For example, International Patent Application WO 99/27852 discloses the use of vacuum pressure and/or heat to increase the availability of interstitial fluid at the area of skin in which the vacuum or heat is applied. The vacuum pressure causes the portion of skin in the vicinity of the vacuum to become stretched and engorged with interstitial fluid, facilitating the extraction of fluid upon entry into the skin. Another method is disclosed wherein a localized heating element is positioned above the skin, causing interstitial fluid to flow more rapidly at that location, thereby allowing more interstitial fluid to be collected per given unit to time.

Still other detection devices have been developed which avoid penetration of the skin altogether. Instead the outermost layer of skin, called the stratum corneum, is "disrupted" by a more passive means to provide access to or extraction of biological fluid within the skin. Such means includes the use of oscillation energy, the application of chemical reagents to the skin surface, etc. For example, International Patent Application WO 98/34541 discloses the use of an oscillation concentrator, such as a needle or wire, which is positioned at a distance from the skin surface and caused to vibrate by means of an electro-mechanical transducer. The needle is immersed in a receptacle containing a liquid medium placed in contact with the skin. The mechanical vibration of the needle is transferred to the liquid, creating hydrodynamic stress on the skin surface sufficient to disrupt the cellular structure of the stratum corneum. International Patent Applications WO 97/42888 and WO 98/00193 also disclose methods of interstitial fluid detection using ultrasonic vibration.

Thus, despite the work that has already been done in the area of minimally invasive analyte testing, there is a continued interest in the identification of new analyte detection methods that are less expensive and eliminate the need for ancillary equipment (e.g., oscillation, suction and heat generating devices). Of particular interest would be the development of a minimally invasive analyte detection system that is inexpensive, easy to use, is integratable into a single component and is safe and efficacious.

Relevant Literature

U.S. patents of interest include: U.S. Pat. Nos. 5,161,532, 5,582,184, 5,746,217, 5,820,570, 5,879,310, 5,879,367, 5,942,102, 6,080,116, 6,083,196, 6,091,975 and 6,162,611. Other patent documents and publications of interest include: WO 97/00441, WO 97/42888, WO 98/00193 WO 98/34541, WO 99/13336, WO 99/27852, WO 99/64580, WO 00/35530, WO 00/45708, WO 00/57177, WO 00/74763 and WO 00/74765A1.

SUMMARY OF THE INVENTION

Percutaneous biological fluid constituent sampling and analyte measurement systems and devices, as well as methods for using the same are provided by the subject invention. A feature of the subject devices is the presence of a constituent transfer medium that samples biological fluid constituents accessed within the skin and transfers at least the target constituent(s) therein to an electrochemical cell for measurement of a at least one targeted constituent, e.g., analyte, within the biological fluid. The present invention finds use in the accessing of biological fluids, such as blood and interstitial fluid, and in the sampling, detection and measurement of various analytes, e.g., glucose, cholesterol, electrolytes, pharmaceuticals, or illicit drugs, and the like. The present invention is especially well-suited for the sampling of interstitial fluid constituents and the measuring of the concentration of glucose within the interstitial fluid.

In general, the subject devices include a skin-piercing or skin-penetrating means, at least one sampling means in the form of a constituent transfer medium, and a measuring means in the form of an electrochemical cell in fluid communication with the constituent transfer medium.

The skin-penetrating means includes at least one hollow micro-needle defining a substantially annular bore or channel through the interior of the micro-needle structure and having an access opening by which the biological fluid is accessed and through which the target analyte(s) enters into the sensor device. In many embodiments, the skin-piercing means comprises an array of such micro-needles.

The electrochemical measurement cell comprises two electrodes in a spaced-apart relationship. The space between the two electrodes defines a reaction zone in which a biological fluid sample is tested for the concentration of a targeted analyte. At least one of the electrodes has a porous structure wherein a first or distal electrode is porous, having at least one pore or hole through the thickness of its planar structure. Each pore or hole is aligned with a micro-needle channel.

In operation, one of the electrodes of the electrochemical cell is used as the reference electrode by which an input reference signal is provided to the sensor from a signal generating means. The other electrode operates as a working electrode that provides an output signal from the cell to a signal receiving means. Preferably, the reference electrode is located at the bottom and the working electrode at the top of the device. This output signal represents the concentration of the target analyte in the sampled fluid.

The constituent transfer medium fills the reaction zone, the pores in the distal electrode and at least a portion of each micro channel. The constituent transfer medium is made of a gel material or matrix that is hydrophilic, i.e., has a high affinity for ionic and anionic particles within biological fluid. Optionally, the gel matrix, also referred to as a hydrogel, may be configured to transfer only particles having a molecular weight less than a specified weight. The gel acts to transfer at least the targeted biological fluid constituent(s) present at the access opening of a micro-needle into the reaction zone. In other words, the targeted constituent(s) migrates through the gel matrix until equilibrium is reached between the concentration of the constituent(s) within the tissue and the concentration of the constituent(s) within the gel matrix. As compared to a hollow micro-needle which relies solely on capillary force that it exerts on the biological fluid as a means to transfer the biological fluid to the electrochemical cell, the subject constituent transfer medium may be configured (i.e., presented in a fully saturated state) to eliminate the transfer of water and other fluids contained within the accessed biological fluid, while transferring only constituents of the biological fluid. It is the configuration of the electrochemical cell that selects the targeted constituent(s) from the remaining constituents for testing.

The subject devices may function as a part of an analyte sensing system that includes a means for controlling the subject devices. Specifically, a control unit is provided in which the control means is electrically coupled with the sensor device and functions to generate and send input signals to the electrochemical cell and to receive output signals from the cell. These functions, among others, may be performed by a software algorithm programmed within the control unit that automatically calculates and determines the concentration of the target analyte in the biological sample upon receipt of an output signal from the electrochemical cell.

Also provided by the subject inventions are methods for using the subject devices and systems as well as kits for use in practicing the devices, systems and methods of the subject invention.

The subject invention is useful for analyte concentration measurement of a variety of analytes and is particularly suited for use in the measurement of glucose concentration in interstitial fluid.

BRIEF DESCRIPTION OF THE DRAWINGS

FIG. 1 includes FIGS. 1A and 1B wherein FIG. 2 is a schematic representation of an exemplary hand-held device for using the biological fluid sensing and analyte measuring devices of the present invention.

DETAILED DESCRIPTION OF PREFERRED EMBODIMENTS

Figure 1A:
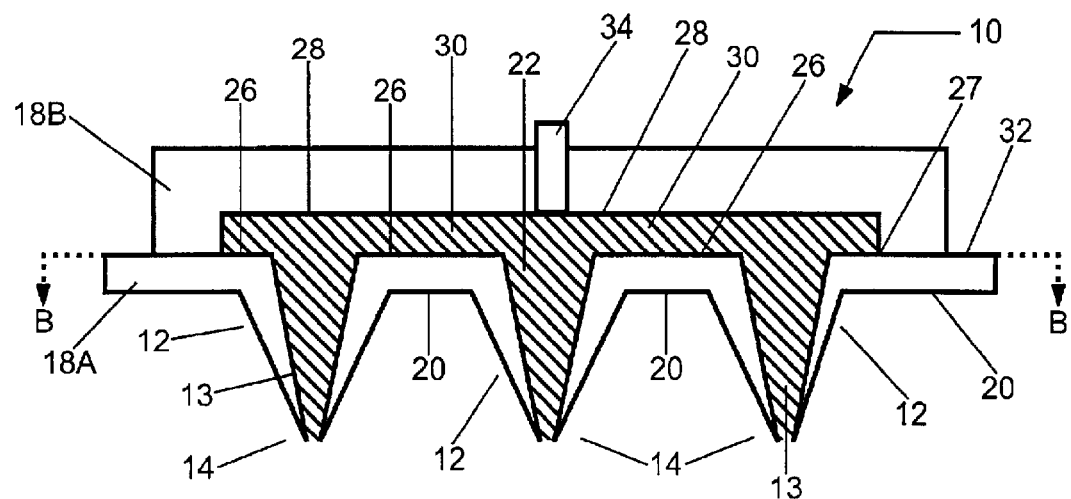
FIG. 1A is a cut-away side view of an exemplary biological fluid sensing and analyte measuring device of the present invention.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any structure and method similar or equivalent to those described herein can also be used in the practice or testing of the present invention, the preferred structure and method of use are now described. All publications mentioned herein are incorporated herein by reference to disclose and describe the structures and/or methods in connection with which the publications are cited.

It must be noted that as used herein and in the appended claims, the singular forms "a", "and", and "the" include plural referents unless the context clearly dictates otherwise. Thus, for example, reference to "a test strip" includes a plurality of such test strips and reference to "the meter" includes reference to one or more meters and equivalents thereof known to those skilled in the art, and so forth.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

Percutaneous biological fluid constituent sampling and measurement devices and systems, as well as methods for using the same, are provided. The present invention finds use in the accessing of biological fluids, such as blood and interstitial fluid, and in the sampling, detection and measurement of a variety of different analytes, e.g., glucose, cholesterol, electrolytes, pharmaceuticals, illicit drugs, and the like.

In general, the subject devices (also referred to as "sensor devices") include a skin-piercing or skin-penetrating means, at least one biological fluid constituent sampling means in the form of a constituent transfer medium, and a constituent concentration measuring means in the form of an electrochemical cell in fluid communication with the constituent transfer medium. In certain embodiments, these components are integrated into a single structure.

The Skin-Penetration Means

The skin-penetration means includes at least one hollow micro-protrusion, e.g., in the form of a micro-needle, defining a substantially annular bore or channel through the interior of the micro-protrusion structure and having an access opening through which biological fluid enters into the sensor device. In many embodiments, the skin-penetrating means comprises an array of such micro-needles.

The subject micro-protrusions or micro-needles are configured to be mechanically stable and strong enough to penetrate the stratum corneum without breaking or flexing. Preferably, they are made of a biocompatible material so as not to cause irritation to the skin or an undesirable tissue response. Although the sensor devices of the subject invention may be disposable, for reusable embodiments, it is preferable that the material of the micro-needles and/or micro-needle arrays is able to withstand sterilization cycles.

The micro-needles and/or the array of micro-needles may be formed of or coated with an insulating material, such as a ceramic, glass, silica, polymer, plastics. Examples of polymers are polyacrylates, epoxies, polyesters polyetheretherketone, liquid crystalline polyesters, or their composites. Examples of ceramics are aluminum oxide, silicon carbide and zirconium oxide. In other embodiments, the micro-needles and/ or the array of micro-needles are made of or coated with a conductive material, such as sintered metal particulate to form a set of electro-sensors. Suitable metallic materials include stainless steel, titanium, precious metals or alloys thereof.

The general configuration of an exemplary sensor device of the present invention will now be described with reference to FIGS. 1A and 1B. In FIG. 1A, there is shown a sensor device 10 having an array 16 of micro-needles 12 separated by skin-contact surfaces 20. Each micro-needle 12 has a sharp open distal tip 14 for easily penetrating through the skin and a channel 13 for accessing and allowing biological fluids to enter into the sensor device 10.

FIG. 1A shows micro-needles 12 have a conically-shaped configuration, but, as will become apparent to one skilled in the art, micro-needles 12 may have any suitable configuration, preferably non-tubular, such as a 3- or 4-sided pyramid configuration for example. The shafts of micro-needles 12 may have an annularly-shaped cross-section or any suitable non-annular cross-section, such as a polygonal shape.

The outer diameter of a micro-needle 12 is generally between about 100 to 400 $\mu$m at the base of the needle, and generally less than about 10 $\mu$m at the tip 14. The average outer diameter of micro-needle 12 is generally between about 100 to 300 $\mu$m and typically between about 120 to 200 $\mu$m. The channel diameter 13 or inner diameter of a micro-needle 12 is generally between about 10 to 200 $\mu$m at the base of the needle.

The length of micro-needles 12 will depend on the desired depth of insertion. More particularly, micro-needles 12 have lengths and sizes within certain ranges depending on the type of biological fluid (e.g., interstitial fluid, blood or both) desired for sampling and the thickness of the skin layers of the particular patient being tested. As such, target skin layers into which the subject skin-piercing means may be inserted include the dermis, epidermis and the stratum corneum (i.e., the outermost layer of the epidermis). In general, micro-needles 12 have a length of at least about 0.05 $\mu$m and more typically at least about 0.1 $\mu$m, where the length may be as great as 500 $\mu$m or greater, but typically does not exceed about 200 $\mu$m and more typically does not exceed about 100 $\mu$m.

As mentioned above, more than one skin-penetrating means may be employed with subject sensor devices. Any suitable number of micro-needles 12 may be employed by the present invention. The optimal number will depend upon various factors including the agent being detected, the body surface location into which the micro-needles are inserted, and the margin of accuracy desired. Regardless of the number micro-needles 12, they are sufficiently separated from each other so as to ensure that the stratum corneum can be penetrated without undue pressure on the skin. In general, micro-needles 12 are separated from adjacent micro-needles a distance, i.e., the length of skin-contact surfaces 20 is generally from about 10 $\mu$m to about 2 mm, typically from about 100 to 1000 $\mu$m, and more typically from about 200 to 400 $\mu$m.

Array 16, including micro-needles 12 and skin-contact surfaces 20, may define a bottom portion 18a of a housing 18, the top portion of which is defined by cover 18b. Housing portion 18a provides a support structure for constituent transfer medium 22 and, as discussed above with respect to micro-needles 12, may be made of insulating or conductive materials. Housing 18b is preferably made of an insulating material such as a plastic or a polymer material to isolate the electrochemical cell.

The Electrochemical Cell

As discussed above, sensor device 10 further comprises measurement means in the form of an electrochemical measurement cell. The electrochemical measurement cell comprises two electrodes in a spaced-apart relationship such that a surface of one electrode faces a surface of the other electrode. Preferably, the electrodes are substantially planar and parallel to each other. The space between the two electrodes defines a reaction zone in which a biological fluid sample is tested for the concentration of a targeted analyte. A redox reagent system or material may be used to facilitate targeting the target analyte(s). The redox reagent material is deposited on at least one of the facing surfaces of the two electrodes whereby biological fluid present in the reaction zone chemically reacts with the reagent material. The particular redox reagent material used is selected based on the analyte targeted for measurement.

At least one of the two electrodes is porous. More particularly, a first or distal electrode is porous, having at least one pore or hole through the thickness of its planar structure. Each pore or hole is aligned with a micro-needle channel such that a fluid pathway is formed from the access opening of the micro-needle, through the micro-needle channel, through the electrode pore and into the reaction zone. The number of pores will depend on the number of micro-needles employed by the sensor device.

The second or proximal electrode may be entirely comprised of a solid conductive material or may have a porous structure, such as a metallized porous material, in which the pores run through the majority of the structure and are much smaller than those of the first electrode. The pore sizes of the second electrode are sufficiently small to create a capillary force on fluid in contact with it thereby causing the fluid within the reaction zone to be drawn or wicked through the second electrode into itself. This configuration facilitates the continuous wicking of the sampled biological fluid and/or constituents therein to within the electrochemical cell thereby purging or displacing air within the cell. The presence of air in the cell can interfere with the analyte measurement. Alternatively, a conventional coplanar electrode pair can be used instead of the top electrode. The subject device may further provide a layer of insulating material over the second electrode for isolating the electrochemical cell and for housing the device. With embodiments having a porous proximal electrode, as just described, one or more vent holes may be formed or made within the housing adjacent the electrode.

Various types of electrochemical systems and methods commonly known in the art of analyte detection and measurement may be employed by the present invention, including systems that are amperometric (i.e., measure current), coulometric (i.e., measure electrical charge) or potentiometric (i.e., measure voltage). Examples of these types of electrochemical measurement systems are further described in U.S. Pat. Nos. 4,224,125; 4,545,382; and 5,266,179; as well as WO 97/18465 and WO 99/49307; the disclosures of which are herein incorporated by reference.

Referring again to the Figures, the electrochemical cell shown in FIG. 1A has a first or bottom electrode 26 and a second or top electrode 28 spaced-apart from each other. The area between electrodes 26 and 28 defines a reaction zone 30 of the cell in which the biological fluid is tested for the concentration of a target analyte(s). The cell may further contain a redox reagent system or material selected based on the particular target analyte(s). As such, the target analyte within reaction zone 30 chemically reacts with the reagent material. At least a portion of the surfaces of the electrodes that face the reaction zone are comprised of a highly conductive material, such as palladium, gold, platinum, silver, iridium, carbon, doped indium tin oxide, stainless steel and the like, or a combination of such materials. The reagent material, comprising an oxidizing enzyme and a mediator component, is deposited on one or both of the facing electrode surfaces.

Electrodes 26 and 28 are preferably substantially parallel to each other to ensure an accurate analyte measurement, and preferably have a substantially planar configuration but may have any suitable configuration or shape such as square, rectangular, circle, etc. The dimensions of the two electrodes are preferably the same, wherein the foot print of each electrode 26, 28 is generally in the range from about 0.1 to 2 cm$^2$ and typically between about 0.25 to 1 cm$^2$. The electrodes are very thin, having a thickness generally in the range from about 50 to 1000 Å, and more typically from about 100 to 500 Å, and more typically from about 150 to 300 Å. The spacing between the electrodes is generally in the range from about 1 to 1000 $\mu$m, and more typically from about 10 to 100 $\mu$m, and more typically from about 10 to 25 $\mu$m.

Figure 1B:
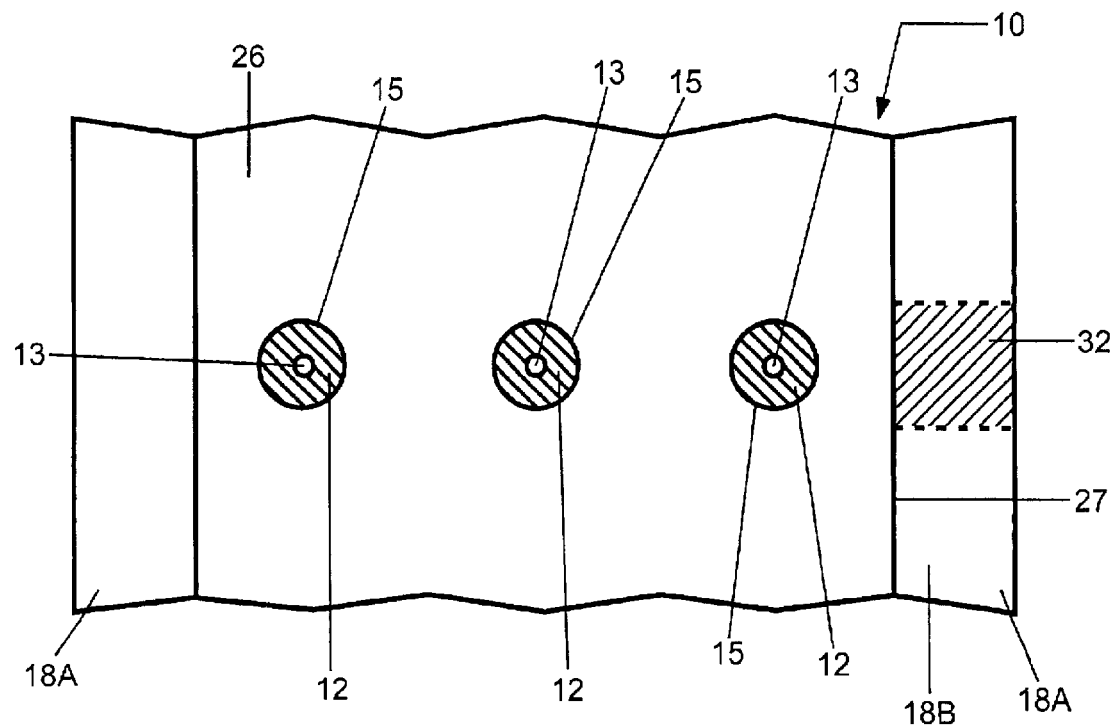
FIG. 1B is a cut-away top view of the device of FIG. 1A taken along arrows b—b.

Referring now to FIG. 1B, first or bottom electrode 26 is structurally supported by the surface area of array 16 between micro-needles 12, i.e., the top surface of the skin-contacting portions 20. A trace of the highly conductive material of first electrode 26 extends laterally outward from an edge 27 (see FIG. 1B) of the surface area of first electrode 26 onto a top surface of bottom housing 18a to provide a first conductive contact 32 for electrically coupling the first electrode 26 to a control unit 52 (discussed below with respect to FIG. 2). Alternatively, first conductive contact 32 can be in the shape of an extended ring. First electrode 26 has spaced-apart pores or holes 15 throughout its surface area. The diameters of pores 15 generally range from about 25 to 200 $\mu$m, typically between about 50 to 150 $\mu$m and more typically between about 100 to 150 $\mu$m.

Second or top electrode 28 may be comprised solely of a non-porous, conductive material formed on the underside of top housing 18b, or of a porous conductive material such as a sintered metallic material. In either case, a metallic insert extends through the thickness of top housing 18b (see FIG. 1A) to provide a second conductive contact 34 for electrically coupling second electrode 28 to a control unit 52 (discussed below with respect to FIG. 2). The size of the pores within a second electrode 28 having a porous configuration generally ranges from about 0.1 to 50 $\mu$m and typically from about 0.1 to 10 $\mu$m. This porous configuration facilitates the continuous wicking of the sampled biological fluid and/or constituent(s) therein to within the electrochemical cell thereby purging or displacing air within the cell through one or more tiny air holes within housing cover 18b (not shown). This is important as the presence of air in the cell can interfere with the analyte measurement.

The Constituent Transfer Medium

In many embodiments, the constituent transfer medium of the sampling means substantially occupies the entire volume of the reaction zone, the pores of the distal electrode and at least a portion of each micro-needle channel, but may substantially or completely occupy the channel to the access opening. The constituent transfer medium is preferably made of a water-based material having a high affinity for water. In many embodiments, the constituent transfer medium is made of a hydrophilic gel material or matrix. The hydrophilic gel helps to precondition the electrodes and reconstitute the reagent material in preparation for the electrochemical measurement of target analytes.

The transfer medium's ability to absorb fluids, particularly water, is dependent upon the extent to which the transfer medium is saturated prior to being exposed to fluid. In order to reduce the time for which the micro-needle is inserted or applied to the skin, the constituent transfer medium is preferably provided in a fully saturated state prior to insertion of the micro-needle into the skin. As such, only the non-fluid constituents, including the one or more targeted constituents, contained within the biological fluid are transferred, thereby eliminating time for the preliminary transfer of biological fluid. As interstitial fluid, for example, is about 98% water, the reduction in diffusion time through the gel may be significant in certain applications.

As between the constituents which are able to diffuse into and through the gel matrix, the speed at which they reach the reaction zone will vary depending on the size of the molecules of the constituents. Generally, the smaller the molecule the faster the diffusion rate through the gel. As many commonly targeted analytes, such as glucose, electrolytes, ascorbic acid, uric acid, etc., have small molecules, these analytes will diffuse through the gel matrix faster than other components of the interstitial fluid comprised of larger molecules.

Suitable gel materials include natural gels made up of naturally occurring polymers, such as agarose, gelatin, mucopolysaccharide, starch and the like, and synthetic gels made up, at least in part, of synthetic polymers, such as anyone of the neutral watersoluble polymers or polyelectrolytes (i.e., synthetic or natural polymers which form ionic charges when dissolved in water), such as polyvinyl pyrrolidone, polyethylene glycol, polyacrylic acid, polyvinyl alcohol, polyacrylamide, and copolymers thereof.

Referring again to the Figures, the gel material of constituent transfer medium 22 resides within and fills at least a portion of micro-needle channels 13 and extends through pores 15 into reaction zone 30. In many embodiments, the gel material completely fills the reaction zone 30 and thoroughly covers and contacts the facing surfaces of first and second electrodes 26, 28, such that there are no air pockets within the gel and within the reaction zone 30. As such, constituent transfer medium 22 provides a pathway for biological fluid constituents to travel from open distal tips 14 to reaction zone 30.

Manufacturing Techniques

An exemplary method of manufacturing the devices of the present invention, such as sensor device 10 of FIG. 1, includes the following steps. A fabrication process known as micro-injection molding may be used to make the bottom housing 18a. First, a mold is provided having the desired physical dimensions of housing 18a and which contains one or more core pins having selected diameters to provide a structure over which to make the micro-needles. As such, the core pins will define the micro-needle channels. The mold is then filled with molten plastic under high pressure and then cooled. Once sufficiently cooled, the core pins are removed, the resulting structure is then ejected from the mold. Materials suitable for making the micro-needles include, but are not limited to, polyetheretherketone, liquid crystalline polyesters, nylons, polyimide, epoxies, polyacrylates, and filled or unfilled thermoplastics. First electrode 26 may then be formed by sputtering a suitable metal or combination of metals, such as those mentioned above in the description of the devices, onto the proximal side of the micro-needles.

Top housing 18b may be molded by means of the micro-injection process explained above. To form top or second electrode 28, a metallic material, such as one or more of those listed above, may be deposited on the bottom surface of housing 18b by sputtering, plasma deposition or electro-deposition techniques, for example. Alternatively, second electrode 28 may be made by injection molding using metal powder. By means of applied pressure, a mixture of gel material is then forced into the pores of the micro-needles. A reagent, specific to the analyte of interest, is deposited onto the top electrode 28. This can easily be accomplished by means of inkjet deposition. The resulting housing portions 18a, 18b may then be sealed together to form sensor device 10. First and second conductive contacts 32 and 34 provide the means for electrically coupling sensor device 10 to control unit such as the hand-held a control unit 52 of FIG. 2. Finally, the micro-needles are filled with a suitable gel material.

Reagents

In order to single out and sense the target analyte or constituent selected for analysis over the other constituents in the sampled biological fluid, a redox reagent is typically employed within the reaction zone within the electrochemical cell. The reagent may reside on the reactive surface of one or both electrodes. Typically this is accomplished by means of an "inkjet" depositing process, as is commonly known in the related art, but other suitable techniques known in the relevant art may also be used.

The reagent comprises one or more enzymes and an optional mediator component. The enzymes used in the invention oxidize the analyte of interest. In many embodiments, the enzyme component of the reagent is an enzyme or a plurality of enzymes that work in concert to oxidize the analyte of interest. In other words, the enzyme component of the reagent system is made up of a single analyte oxidizing enzyme or a collection of two or more enzymes that work in concert to oxidize the analyte of interest. Enzymes of interest include oxidases, dehydrogenases, lipases, kinases, diaphorases, quinoproteins and the like. The specific enzyme present in the reaction area depends on the particular analyte for which the electrochemical test device is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many embodiments where the analyte of interest is glucose, the enzyme component of the reagent system is a glucose-oxidizing enzyme (e.g., a glucose oxidase or glucose dehydrogenase). The amounts of the various components may vary, where the amount of enzyme component typically ranges from about 0.1 to 10% by weight.

An optional second component of the reagent system is a mediator made up of one or more mediator agents. A variety of different mediator agents are known in the art and include: ferricyanide, phenazine ethylsulphate, phenazine methylsulfate, phenylenediamine, 1-methoxy-phenazine methylsulfate, 2,6-dimethyl-1,4-benzoquinone, 2,5-dichloro-1,4-benzoquinone, ferrocene derivatives, osmium bipyridyl complexes, ruthenium complexes and the like. In those embodiments where glucose is the analyte of interest and glucose oxidase or glucose dehydrogenase is the enzyme components, mediator of particular interest is ferricyanide. Other reagents that may be present in the reaction area include buffering agents, (e.g., citraconate, citrate, phosphate), "Good" buffers and the like.

The Sensor System

In the sensor system of the present invention, the reference and working electrodes are in electrical communication with a control means that sets the input reference signal transmitted to the electrochemical cell, receives the output signal from the electrochemical cell and then derives the concentration level of the targeted analyte(s) within the accessed biological fluid from the output signal, e.g., a means for applying an electrical current between the two electrodes, measuring a change in the current over time and relating the observed change in current to the concentration of analyte present in the electrochemical cell. The concentration of the analyte in the patient's blood is then derived from the concentration level in the biological fluid accessed, the numerical value of which may be provided as an output signal to a display means.

In certain embodiments, the control and display means are integrally housed within a hand-held control unit such as that illustrated in FIG. 2. The control unit preferably also provides a means of securing or holding one or more micro-needles or an array of micro-needles in a position and arrangement suitable for the particular sampling and measuring application at hand.

Referring now to FIG. 2, there is shown a representation of a sensor system 50 of the subject invention. Sensor system 50 comprises a hand-held control unit 52 and a sensor device such as device 10 of FIG. 1 operatively mounted to distal end 54 of control unit 52. Control unit 52 has a housing 56, preferably made of a medical grade plastic material or the like, having a low-profile configuration which houses a means (not shown) for controlling the measurement means of sensor device 10, i.e., generating and transmitting input reference signals to the electrochemical cell of device 10 and receiving output measurement signals from the cell. A software algorithm programmed within control unit 52 automatically calculates and determines the concentration of the target analyte in the biological fluid accessed upon receipt of the output signal. The concentration level (among other desired information) is then transmitted to an external display means or screen 58 that displays information to the user. Control interface buttons 60 allow the user to input information to the control means, such as the type of analyte targeted for measurement.

Sensor device 10 is electrically and physically coupled to control unit 52. Electrical communication between the two is established by means of conductive contacts 32 and 34 on device 10, described with respect to FIG. 1, and corresponding electrical traces (not shown) within control unit 52. Preferably, device 10 and control unit 52 are physically coupled by a quick lock-and-release mechanism (many of which are commonly known and understood) such that a used sensor device can be easily removed and replaced. Control unit 52 is preferably reusable and usable with any number of sensor devices of the subject invention. These features facilitate the taking of multiple samples and measurements in an efficient and rapid manner.

A device such as control unit 52 which automatically calculates and determines the concentration of a selected analyte in biological fluid and/or in the patient's system, such that a user need only insert a micro-needle of the subject invention into the patient's skin and then read the final analyte concentration result from a display of the device, is further described in U.S. Pat. No. 6,193,873 entitled "Sample Detection to Initiate Timing of an Electrochemical Assay," the disclosure of which is herein incorporated by reference.

Methods of Use

Also provided by the subject invention are methods for using the subject devices and systems to determine the concentration of an analyte in a physiological sample. A variety of different analytes may be detected using the subject sensor systems, where representative analytes include glucose, cholesterol, lactate, alcohol, and the like.

In practicing the subject methods (with reference to the Figures), the first step is to provide a sensor 10, preferably particularly configured (i.e., containing the appropriate reagent) for targeting the analyte(s) of interest. The sensor 10 may be operatively engaged and interfaced with a control unit 52 that can be manually held and controlled by the user. Control unit 52 is programmed for testing the targeted analyte(s). The user positions sensor 10 over a selected area of the patient's skin, and, with slight pressure, the micro-needle(s) 12 of sensor device 10 are caused to penetrate into the skin. The depth to which the micro-needles 12 are inserted will depend on the length of the respective micro-needles or by some other means associated with the sensor unit 10 for limiting the insertion depth.

Upon insertion into the patient's skin, an amount (i.e., a sample) of at least the target constituent(s) within the biological fluid present at the open tips 14 of micro-needles 12 is caused to enter through open tips 14 into channels 13 of the respective micro-needles by means of a diffusion mechanism due to the concentration gradient of the hyrdrogel. The sampled constituents continue to be absorbed by the gel and to diffuse in a proximal direction through channels 13, through pores 15 of first electrode 26 and into reaction zone 30. Once in the reaction zone 30, the targeted constituent(s) or analyte(s) chemically reacts with the selected reagent(s) to form electroactive products. The electroactive products are then either oxidized or reduced by the optional mediator or directly by the working electrode 28. The resulting output signal level is then conducted to the control unit by electrode 28. A software algorithm programmed within control unit 52 then automatically determines the differential between the output and reference signals, derives the concentration of the targeted analyte(s) in the biological fluid accessed from this differential value, and then derives the corresponding concentration level of the selected analyte(s) in the patient's blood. Any or all of these values may be displayed by display means or screen 58.

Kits

Also provided by the subject invention are kits for use in practicing the subject methods. The kits of the subject invention include at least one subject sensor device having one or more micro-needles of the subject invention. The kits may also include a reusable or disposable control unit that may be used with reusable or disposable sensor devices of the kit or from other kits of the subject invention. These kits may include sensors having an array of micro-needles having the same or different lengths. Certain kits may include various sensors each containing the same or different reagents. Also, more than one reagent may be provided within a single micro-needle array, wherein one or more of the micro-needles are provided with a first reagent for testing a first target analyte and one or more other micro-needles are provided with other reagents for testing other targeted analytes. Finally, the kits preferably include instructions for using the subject sensors in the determination of an analyte concentration in a physiological sample. These instructions may be present on one or more of the packaging, a label insert, or containers present in the kits, and the like.

It is evident from the above description that the subject inventions are easy to use, eliminating ancillary components for enhancing the amount or velocity of fluid flow within the skin in order to compensate for the negative pressures within the skin. Additionally, the subject inventions provide for the rapid exchange and replacement of sensors, reducing the time necessary for each sampling and measurement activity which is particularly advantageous when administering multiple tests on a single patient or having to test many patients consecutively. As such, the subject invention represents a significant contribution to the field.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

Although the present invention is useful for many applications, the sampling of various biological fluids and the detection of many types of analytes, the invention has been described primarily in the context of the detection of analytes in interstitial fluids, and as being particularly useful for the detection of glucose in interstitial fluid. Thus, the specific devices and methods disclosed and the applications, biological fluids and analytes discussed herein are considered to be illustrative and not restrictive. Modifications that come within the meaning and range of equivalents of the disclosed concepts, such as those which would readily occur to one skilled in the art, are intended to be included within the scope of the appended claims.

What is claimed is:

1. A biological fluid constituent sampling and concentration measurement device, said device comprising:
   at least one skin-piercing member comprising a proximal end, a distal end, a channel extending from the proximal end to the distal end and a biological fluid access opening at the distal end;
   an electrochemical cell for measuring the concentration of analyte within the biological fluid, wherein the cell comprises a first planar electrode positioned substantially transverse to the at least one skin piercing member and comprising a hole axially aligned with the channel of the at least one skin-piercing member; and a constituent transfer medium comprising a hydrophilic material in fluid communication with the channel of the at least one skin-piercing member and with the at least one planar electrode.

2. The device of claim 1 wherein the hydrophilic material comprises a gel matrix.

3. The device of claim 2 wherein the gel matrix comprises a natural gel.

4. The device of claim 3 wherein the natural gel is selected from the group comprising agarose, gelatin, mucopolysaccharide, starch and the like.

5. The device of claim 2 wherein the gel matrix comprises a synthetic gel.

6. The device of claim 5 wherein the synthetic gel comprises a neutral water-soluble polymer.

7. The device of claim 2 wherein the synthetic gel comprises a polymer.

8. The device of claim 7 wherein the polymer is selected from the group consisting of polyvinyl pyrrolidone, polyethylene glycol, polyacrylic acid, polyvinyl alcohol, polyacrylamide, and copolymers thereof.

9. The device of claim 1 wherein the electrochemical cell further comprises a second planar electrodes spaced a from the first planar electrode wherein a reaction chamber is defined there between.

10. The device of claim 9 wherein the distance between the electrodes is from about 50 to 1000 Å.

11. The device of claim 10 wherein the distance between the electrodes is from about 100 to 500 Å.

12. The device of claim 9 further comprising at least one reagent material for chemically reacting with at least one biological fluid constituent, the at least one reagent material located on a surface of at least one electrode facing the reaction chamber, wherein the at least one reagent is selected based on the at least one constituent targeted for measurement.

13. The device of claim 9 wherein the second electrodes is porous and the pores of the second electrode are substantially smaller than the hole in the first electrode.

14. The device of claim 13 further comprising a housing halving at least one vent hole for venting air from within the electrochemical cell.

15. The device of claim 1 wherein the biological fluid interstitial fluid and the analyte is glucose.

16. A kit for sampling biological fluid constituents from the skin of a patient and for measuring the concentration of at least one analyte within the sampled biological fluid constituents, the kit comprising a plurality of devices according to claim 1.

17. The kit of claim 16 wherein the plurality of devices is disposable.

18. A system for sampling biological fluid constituents from the skin of a patient and measuring at least one target constituent within the sampled biological fluid constituents, the system comprising:

(a) at least one device according to claim 1; and (b) a control means in electrical communication with the at least one device, the control means comprising:

(1) means for sending an electrical input signal to the device and for receiving an electrical output signal from the device, and (2) a software algorithm which automatically calculates and determines the concentration of the target analyte in the accessed biological fluid upon receipt of the electrical output signal.

19. A method for sampling biological fluid constituents within the skin of a patient and for measuring the concentration of one or more target analytes contained therein, the method comprising the steps of:

providing a system according to claim 18;

operatively applying a first device to the patient's skin wherein the system samples the patient's biological fluid constituents and measures the concentration of the one or more target analytes therein;

removing the first device from the patient's skin;

removing the first device from the, control means;

operatively coupling a second device to control means; and repeating the above steps until the desired number of samplings and measurements have been performed.

20. The system of claim 18 further comprising a display means in electrical communication with the control means for displaying information in the form of electrical signals received from the control means related to the sampling of the at least one biological fluid constituents and the measuring of the at least one target constituent.

21. The system of claim 20 wherein the device is mounted to the housing by means of a lock-and-release mechanism.

22. A kit for sampling biological fluid constituents from the skin of a patient and for measuring the concentration of at least one analyte within the sampled biological fluid constituents, the kit comprising:

a system according to claim 18.

23. The kit of claim 22 wherein the control means is reusable.

24. The kit of claim 23 wherein the at least one device comprises two or more reagent materials for testing two or more targeted analytes.

25. The system of claim 18 further comprising a housing wherein the control means is located within the housing and the device is mounted to the housing.

26. The system of claim 25 further comprising user input buttons on the housing for providing user input to the control unit.

27. The system of claim 25 further comprising a display means on the housing for displaying information from the control means.

28. The system of claim 25 wherein the housing has a hand-held configuration.

29. A method for accessing a biological fluid within the skin of a patient the method comprising the steps of:

providing at least one micro-needle comprising an open distal end and a channel therethrough;

inserting the at least one micro-needle into the skin to a selected depth;

absorbing through the open distal end and into the micro-needle channel constituents present within biological fluid present at the open distal end; and transferring the absorbed constituents through a hole in a conductive material into a measurement chamber, wherein the conductive material is substantially transverse to the at least one micro-needle and the hole is axially aligned with the micro-needle channel.

30. The method according to claim 29 further comprising the steps of:

exerting a capillary force on the sampled biological fluid present in the measurement chamber; and transferring the sampled constituents through a second conductive material comprising pores having a size substantially smaller than the hole.

31. The method according to claim 30 further comprising the step of venting air from the measurement chamber.

32. The method of claim 29 further comprising the steps of:

causing the sampled constituents to chemically react with a selected reagent within the measurement chamber;

providing a first signal to the measurement chamber; and receiving a second signal from the measurement chamber, wherein the second electrical signal is representative of the concentration of the target analyte in the accessed biological fluid.

33. The method according to claim 32 wherein the accessed biological fluid is interstitial fluid and the at least one target analyte is glucose.

34. The method of 32 further comprising the step of deriving the concentration level of the at least one target analyte in the patient's blood from the second signal.

35. The method of claim 34 further comprising the step of displaying a numerical value representative of the concentration of the at least one target analyte in the patient's blood.

36. The method according to claim 35 wherein the step of deriving comprises using a software algorithm.

* * * * *

UNITED STATES PATENT AND TRADEMARK OFFICE
CERTIFICATE OF CORRECTION

PATENT NO. : 6,875,613 B2
DATED : April 5, 2004
INVENTOR(S) : Robert Shartle et al.

It is certified that error appears in the above-identified patent and that said Letters Patent is hereby corrected as shown below:

Column 13,
Line 25, please replace the word "a" after the word "spaced" and before the word "from" with the word -- apart --.
Line 43, please replace the word "halving" before the word "at" with the word -- having --.

Signed and Sealed this

Twenty-eighth Day of June, 2005

JON W. DUDAS
*Director of the United States Patent and Trademark Office*